(12) United States Patent
Hall et al.

(10) Patent No.: US 10,123,784 B2
(45) Date of Patent: Nov. 13, 2018

(54) IN SITU SPECIMEN COLLECTION RECEPTACLE IN A TOILET AND BEING IN COMMUNICATION WITH A SPECTRAL ANALYZER

(71) Applicant: David R. Hall, Provo, UT (US)

(72) Inventors: David R. Hall, Provo, UT (US); Joshua Larsen, Spanish Fork, UT (US); Jared Reynolds, Provo, UT (US); Dan Allen, Springville, UT (US); Joe Fox, Spanish Fork, UT (US)

( * ) Notice: Subject to any disclaimer, the term of this patent is extended or adjusted under 35 U.S.C. 154(b) by 237 days.

(21) Appl. No.: 14/944,738

(22) Filed: Nov. 18, 2015

(65) Prior Publication Data
US 2017/0135677 A1    May 18, 2017

(51) Int. Cl.
| A61B 10/00 | (2006.01) |
| E03D 9/00 | (2006.01) |
| E03D 13/00 | (2006.01) |

(52) U.S. Cl.
CPC .............. *A61B 10/007* (2013.01); *E03D 9/00* (2013.01); *E03D 13/005* (2013.01)

(58) Field of Classification Search
CPC .................................................... A61B 10/007
USPC ....................................................... 73/864.51
See application file for complete search history.

(56) References Cited

U.S. PATENT DOCUMENTS

| 5,313,672 A * | 5/1994 | Luedtke ..................... E03D 9/00 4/144.1 |
| 2005/0261605 A1* | 11/2005 | Shemer ................. A61B 10/007 600/573 |
| 2009/0086202 A1* | 4/2009 | Wang ........................ G01J 3/02 356/301 |
| 2015/0173937 A1* | 6/2015 | Jackson ................ A61F 5/4405 604/318 |
| 2015/0359522 A1* | 12/2015 | Recht ...................... G01N 33/62 600/573 |
| 2017/0307512 A1* | 10/2017 | Akagawa ............. G01N 33/493 |

FOREIGN PATENT DOCUMENTS

KR        20100004273 A  *  1/2010  ........... A61B 10/007

* cited by examiner

*Primary Examiner* — Walter L Lindsay, Jr.
*Assistant Examiner* — Philip Marcus T Fadul

(57) ABSTRACT

A specimen collection receptacle formed by a channel disposed within the wall of a toilet bowl. The receptacle is located above the weir water line. The receptacle comprises a channel open to the interior of the bowl having opposed non-parallel side walls. The side walls may be joined opposite the opening. The side walls may be joined by a bottom wall. The bottom wall may be arcuate. The side walls may be non-planar. The walls may exhibit a roughened surface. The receptacle may comprise an optical window. The receptacle may comprise a cuvette. The receptacle may be in communication with one or more light emitting probes. The receptacle may be self-cleaning. The receptacle may comprise a replaceable module disposed in the wall of the toilet bowl. The receptacle may be located at the front of the toilet bowl. The receptacle may be disposed in a toilet bowl liner or insert.

20 Claims, 4 Drawing Sheets

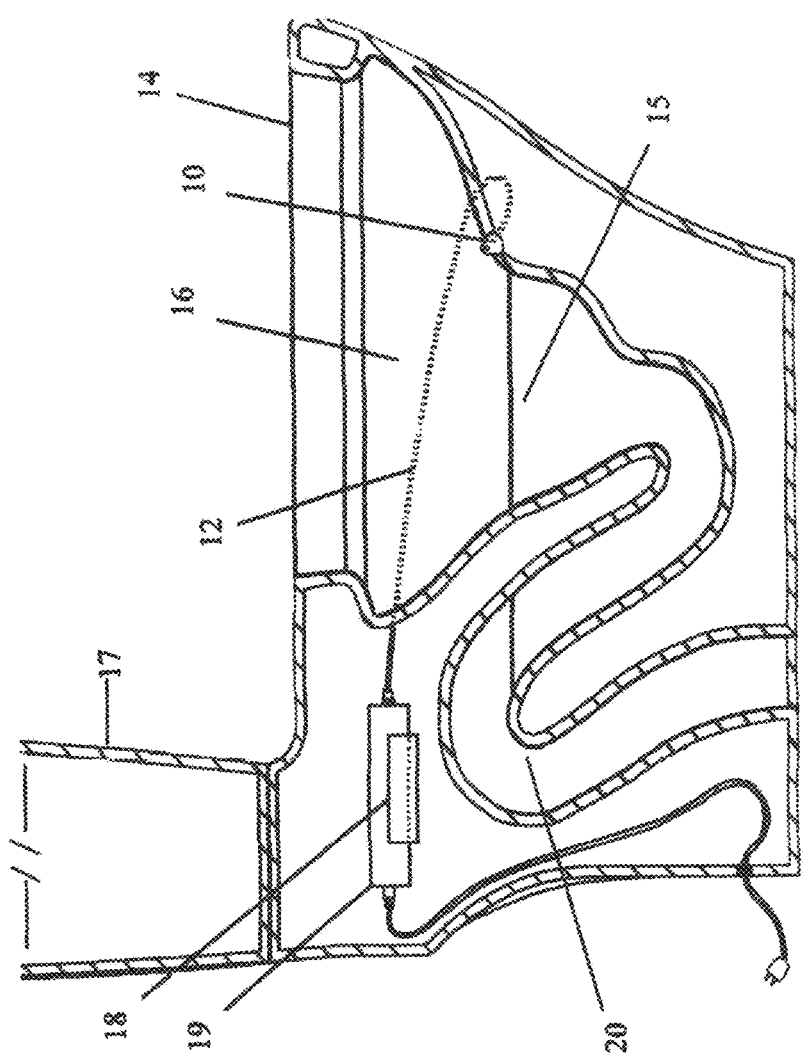

IN SITU SPECIMEN COLLECTION RECEPTACLE IN A TOILET AND BEING IN COMMUNICATION WITH A SPECTRAL ANALYZER

FIELD OF INVENTION

This disclosure relates to the field of specimen collection receptacles for analyzing samples in situ. More particularly, this disclosure teaches a collection receptacle disposed within the wall of a human waste disposal appliance, such as a toilet, urinal, or pot. The walls of the collection receptacle are configured to capture a sufficient sample and retain it long enough for in situ analysis by sensors or probes connected to the receptacle and then release the sample in the ordinary course of cleansing the receptacle.

BACKGROUND

Human waste contains an unparalleled amount o health-related information. In particular, urine is routinely analyzed by healthcare professionals to obtain information regarding an individual's disease state, hormonal balance, nutritional status, pharmaceutical use, metabolic activity, microbial balance, risks of future health complications and other clinical points of interest. Conventionally, this information is obtained following sample submission to a laboratory; however, laboratory analysis typically only provides single-point data and is often a lengthy and awkward process for patients. Since human health is not an isolated event, the health information provided by the current testing methodology offers mere glimpses into an individual's health status. Ideally, key health measures would be assessed on an ongoing basis; however, the cost and inconvenience of laboratory analysis make regular testing prohibitive for the majority of people. In contrast, an on-site, in situ urine collection and analysis unit capable of delivering accurate, continuous and minimally invasive health testing would offer unprecedented longitudinal health-related information to individuals and healthcare professionals. Such in situ sample collection and analysis is most conveniently achieved at the typical site of urine excretion: the toilet, urinal, or pot.

Urine collection methods designed for on-site urine analysis have been described previously. For example, U.S. Pat. No. 5,073,500 (hereafter referred to as reference 1, the entire disclosure of which is incorporated herein by this reference) describes a toilet apparatus which measures the concentrations of urinary components based on the specific wavelength-absorbing characteristics of a urine sample following passage through a liquid chromatograph. Urine is collected in a large funnel located at the front of the toilet bowl that channels samples into an automated liquid chromatography system, where it is separated into sample aliquots by gas injection, combined with a urinary component-specific reagent, forced through a liquid chromatograph and then exposed to a component-specific wavelength of light. The system is neither convenient nor practical for unassisted personal use.

A more practical approach to analysis is described U.S. Pat. No. 5,772,406 (hereafter referred to as reference 2, the entire disclosure of which is incorporated herein by reference), which describes a toilet stool-based spectroscopic system that analyzes uric component concentrations by measuring urine sample absorbance of select wavelengths of visible or near-infrared light. In this system, a urine collecting basin is located in the front of a toilet bowl. Urine that enters the basin passes through a screen into a tube, where it is held back by a valve. When the system is ready process urine, the valve opens and urine flows down the tube through a spectral analysis cell to a closed secondary valve. A liquid sensor determines whether sufficient urine has been captured to fill the spectral analysis cell. If so, analysis is conducted. Following the analysis, the secondary valve is opened and the urine is evacuated to the sewage system. The system then undergoes a flush cycle which is monitored by a sensor to insure that the urine collecting part and the spectral analysis cell are sufficiently clean to assure valid analytical results. This is accomplished using a washing solution that is discharged front a nozzle located opposite to the urine collecting basin. Once the spectral analysis cell is sufficiently clean, a cell blank measurement of the empty cell or of a water-filled cell is taken to establish a clean reference for the next sample.

Other creative methods employed for sample capture and analysis include U.S. Pat. No. 5,730,149 (hereafter referred to as reference 3, the entire disclosure of which is incorporated herein by reference), which describes an extensible, mechanically operated collection spoon. Following extension of the collection device, urine is captured mid-air and is forwarded via a flexible tube through the swing arm and spindle to the urinalysis device, where reagents are added to the sample for component quantification. U.S. Pat. No. 7,812,312 (hereafter referred to as reference 4, the entire disclosure of which is incorporated herein by reference) describes a system for analysis of aqueous systems using, attenuated total reflectance (ATR) crystals. In a toilet embodiment of the invention, the ATR body is preferentially designed as a flow-through cell with a reversibly closeable inlet and outlet incorporated into a separate sampling line branching from the toilet drain pipe.

Perhaps the most feasible in-toilet urine collection approach is outlined in U.S. Pat. No. 5,815,260 (hereafter referred to as reference 6, the entire disclosure of which is incorporated herein by reference), which describes a toilet stool-based analytical system that measures the concentrations of erogenous components using Raman spectroscopy. Urine is collected in a frontal basin which is connected to a light-emitting fiber optic cable and a light-receiving fiber. The light-emitting cable transmits light from a laser source across the basin and through the sample to the light-receiving cable which conducts the resultant light to a Raman spectrometer. Following spectral analysis, the basin is cleared by flush water and drained through a scupper to prepare the basin for a new collection and sampling procedure.

Unfortunately, previous attempts to facilitate automated urine specimen collection, preparation and analysis are hindered by mechanical complexity and difficulties in creating a spectral sampling pathlength of appropriate thickness that is also amenable to rapid sample evacuation and easy cleaning. For example, when sampling a liquid such as urine which is predominantly comprised of water with near-infrared spectroscopy, a transmission sample pathlength of 1 mm is necessary to obtain useitil results. While urine will flow through a gap of this size, the rate of flow is significantly hindered, and passage of a typical 300-800 mL sample of urine through such a space is unacceptably slow. Furthermore, expulsion of fecal matter into the collection unit represents a significant obstacle for quality analysis, especially if the fecal matter becomes lodged inside a collection tube with a 1 mm sampling area. In overcoming these obstacles, it is an object of the present invention to provide an automated urine specimen collection device capable of channeling urine through a spectral analysis site with a pathlength appropriate to the demands of the chosen spectrometer without significantly impinging the overall flow of urine or subsequent flush cycle. Additionally, the unit will be able to maintain a clean environment suitable to high quality spectral analysis. In so doing, the present invention allows for elegant in situ urine sampling and analysis.

SUMMARY OF THE INVENTION

The present invention describes a receptacle for the in situ collection, preparation and analysis of urine samples within the toilet bowl cavity. Urine is excreted into the toilet bowl or a toilet insert and channeled by flow-directing protrusions towards a vertically oriented spectral flow cell. Urine passing through the flow cell or retained by the flow cell is optimally situated for spectral assessment. Light is transmitted through the sample from a light-emitting probe to a light-receiving probe and passed to a spectrometer for assessment.

BRIEF DESCRIPTION OF THE DRAWING

FIG. 3 is a diagram of a sectional view of the toilet.

DETAILED DESCRIPTION OF THE PREFERRED EMBODIMENTS

Figure 1:
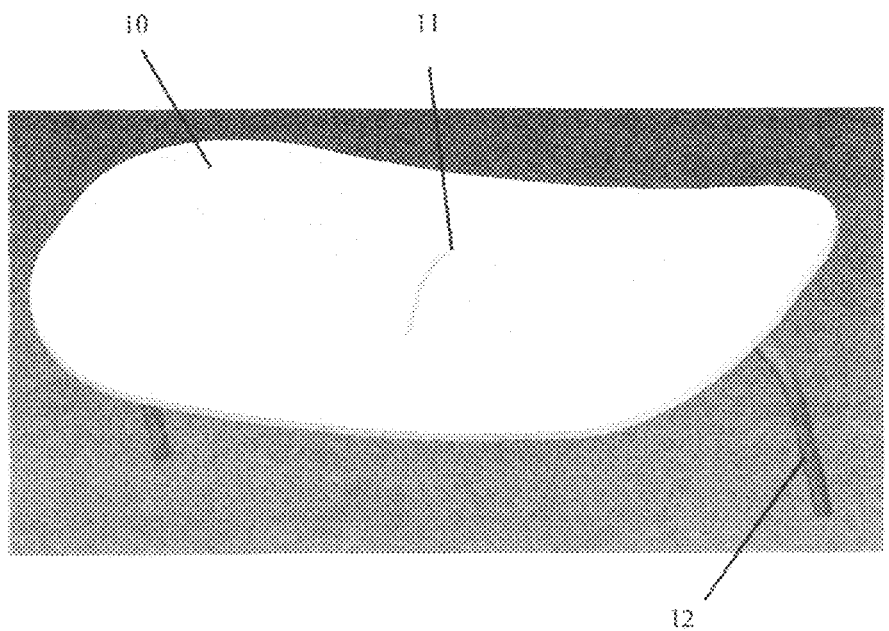
FIG. 1 is a diagram of the in situ specimen collection receptacle comprising an analysis channel or flow cell.

FIG. 1 is a diagram of the in situ specimen collection receptacle 10 comprising an analysis channel or flow cell 11. The receptacle is connected to a spectro analyzer (FIG. 3 19 and transmission device 18) by fiber optic cables 12.

Figure 1A:
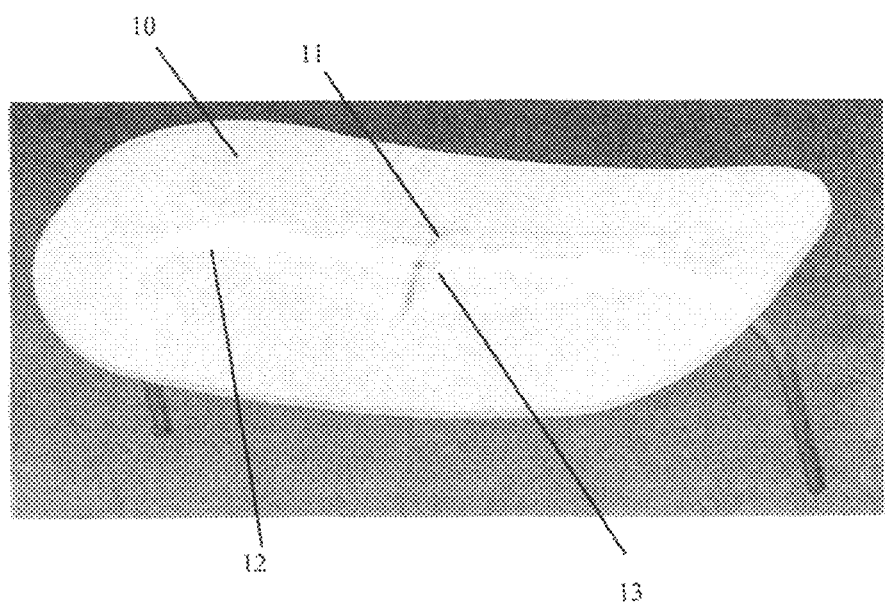
FIG. 1a is a transparent view of FIG. 1 which depicts the positioning of the fiber optic cables relative to the analysis channel or flow cell.

FIG. 1a is a diagram of the in situ specimen collection receptacle as shown in FIG. 1a further depicting the fiber optic cables 12 in communication with the analysis channel or flow cell 11 at a fiber optic cable interface 13 that may include light emitting and light receiving cable ends, collimating lenses, or a spectral window.

Figure 2:
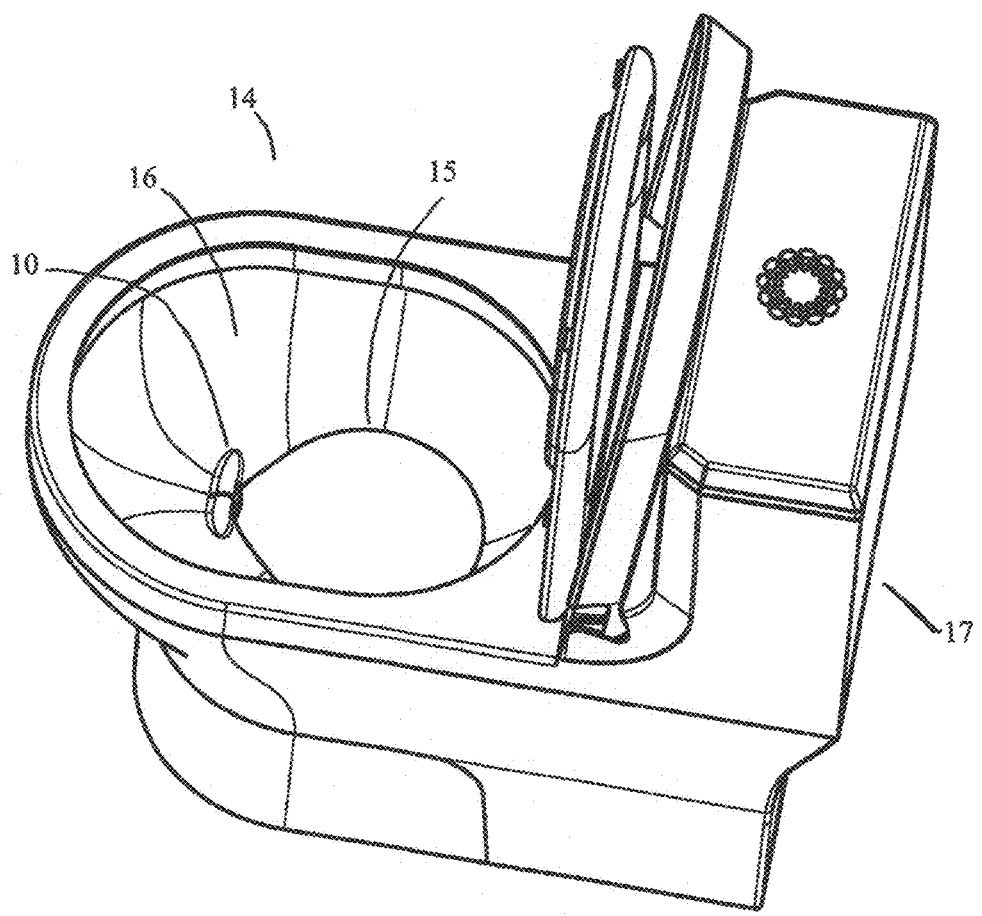
FIG. 2 is a depiction of a collection device disposed within a toilet bowl.
Figure 4A:
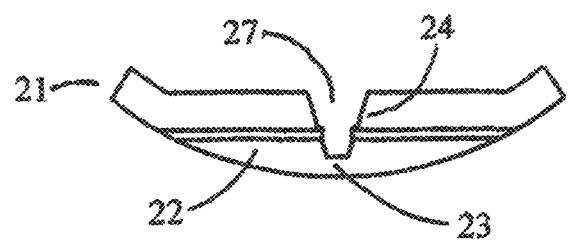
FIGS. 4a-4d are cross-sectional views of the analysis channel or flow cell configurations.
Figure 4B:
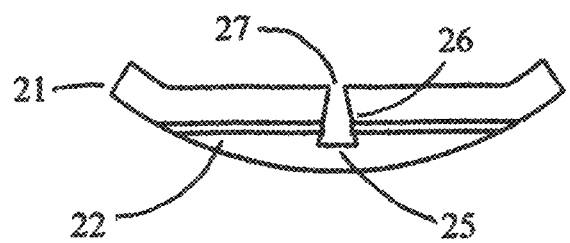
Figure 4C:
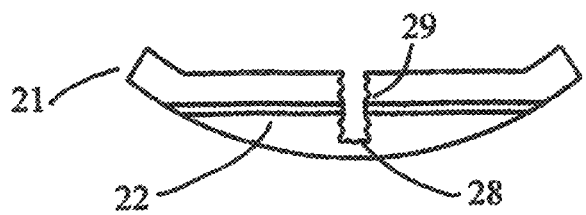
Figure 4D:

FIG. 2 is a diagram of a floor mounted toilet 14 comprising a water supply tank 17 a bowl 16 and a weir water line 15. Also depicted is the analysis channel 10 located above the weir water line.

FIG. 3 is a diagram of a longitudinal sectioned view of the toilet 14. The toilet comprises a water supply tank 17, a bowl 16, a weir 20, and weir water line 15, the collection receptacle 10 connected by means of a fiber optical cable 12 to a spectral analyzer 19 and transmission device 18. The spectral analyzer is connected to a monitor that is not shown. The collection receptacle 10 may be located at the front of the bowl 16. The front surface of the bowl 16 may be inclined. The location of the collection receptacle 10 should be convenient fur both male and female urination events. Also, the location should be above the weir water line 15. Water from the tank 17 that enters the bowl 16 during the flush cycle may be used to cleanse the analysis channel 11 and the fiber optic cable interface 13. Additionally, a cleansing solution may be added to the tank's water supply to insure adequate cleansing. The cleansing solution may be applied to the channel 11 from a nozzle, not shown, positioned in the bowl wall 16 and directed toward the channel 11.

FIGS. 4a-4d are cross-sectional diagrams 21 of the receptacle 10. The analysis channel's opposed walls 24, 26, and 30 feature non-parallel configurations. Side wall 24 form a truncated cone shape; side wall 26 form reentrant side walls, and side walls 30 are curvilinear, such as convex or concave. Channel wall 29 features a non-planar surface. The variety of wall configurations and surface finishes are intended to control the sample flow through the analysis channel 11, maximize sample volume, promote capillary adhesion of the sample during analysis, restrain ambient light, and facilitate cleansing. The volume of the analysis channel 11 should be about at least 5 mL. The volume of the channel 11 proximate the cable interface 13 should be at least 150 µL and not more than 2 mL. Preferably, the volume should be around between 300 µL and 600 µL. The actual volume proximate the cable interface 13 may vary depending on the nature of the analysis and the equipment used.

In the preferred embodiment, urine is excreted by the user into a toilet bowl 16 or a toilet insert and flows down to the urine specimen collection receptacle 10 which lies flush with the surface of the toilet bowl 16 or insert. Protrusions from the surface of the collection receptacle direct urine flow towards the analysis channel or flow cell 11. Excess urine overflows the protrusions and drains into the reservoir of the toilet bowl or insert 16, leaving a tiny pool of urine that gravimetrically feeds through the analysis channel or flow cell 11. Once flow through the cell has ceased, the capillary effect ensures that a residual amount of urine fills the flow cell 11, covering the light transmission site 26. Either during the flow-through period or after capture of a sample via the capillary effect, light is transmitted through the sample from a light-emitting fiber optic cable 12 to a light-receiving fiber optic cable 22. Light captured by the light-receiving cable 22 then passes down the fiber optic cable to the spectrometer 19, where it is reflected, diffracted and focused onto a photodetector to generate spectral data on the urine sample using the transmission device 18. When the toilet is flushed, water from the flush cycle is again channeled to and through the flow cell 11, displacing the urine and allowing it to exit with the rest of the bodily waste.

In one embodiment, the analysis channel 1 comprises a vertically-oriented gap 27 open to the bowl 16. This gap 27 is of a width that best fits the spectral path length requirements of the requisite spectrometer(s) and may range from 0.01-1.3 mm, with a preferred width of 0.5-2 mm. For example, in one embodiment, a gap 27 of 1 mm provides the ideal pathlength for a urine sample when the channel 11 is coupled with a near-infrared spectrometer. Fiber optic cables 12, 22 with core sizes ranging from 0.1-1,000 µm, with the preferred core size ranging from 1-600 µm, are placed in close proximity to the edge of the gap 27. Preferentially, these will be multi-mode fibers. Both fibers need not have the same configuration or core size. Furthermore, the cables 12, 22 will have a maximum angle of curvature which cannot be exceeded and may be contained within a stable housing to ensure an optimal radial conformation. Alternatively, the light-emitting or light-receiving elements of the flow cell 11 may be placed in a straight, direct alignment with the light source or spectrometer 19. The surface of the gap 27 will preferentially contain one or more optical elements 13 such as cable ends, collimating lenses or a spectral window. These optical elements may be formed from any arbitrary material which is transparent to the radiation employed by the spectrometer light source, especially to electromagnetic radiation in the ultraviolet, visible, near-infrared or middle infrared regions. Alternatively, the entirety of the collection receptacle 11 may be formed from an optic material to provide a seamless optic environment. The presence and type of these flow cell components is conditional on the specific requirements of the spectrometer and sampling techniques.

In an embodiment, the analysis receptacle 11 exhibits non-parallel side walls 24, in order to maximize the volume of the channel 11, promote sample retention, and post analysis cleansing. In another embodiment that side walls 26 may exhibit a reentrant configuration in order to control ambient light that may iaterfert with the spectral analysis. Other embodiments may comprise non-planar side walls 29 comprising corrugations, channels, discontinuities, or protrusions to control sample flow and aid in retention of the sample during analysis. And the side walls 30 may be curvilinear, such as concave or convex, in order to accommodate the spectral analysis, facilitate cleaning, and sample retention. It may be desirable that the side walls 24, 26, 29 and 30 comprise a combination of features as disclosed herein. The bottom walls 23, 25, and 28 may incorporate the features of the other side walls. The bottom wall may be stepped as a means for controlling the flow of the sample through the channel 11. Baffles may be added to the channel 11 for sample retention and control. The channel 11 may not have a bottom wall 23, 25, and 28 when it is desirable to have the side walls converge at the bottom forming a V shaped channel. The walls 23, 24, 25, 26, 28, 29, and 30 may comprise a replaceable insert to facilitate cleaning and maintenance. The insert could be fashioned so as not to interfere with the light emitting or receiving ends of the fiber optic cables 12, 22. At least a portion of the walls may exhibit a polished surface, even a mirror polished surface, in order to promote capillary adhesion and cleansing. For example only the proximal region of the channel 11, the region before the spectral window or fiber optic cable interface 13, may be polished while the distal region of the channel 11, the region after the spectral window or fiber optic cable interface, could be non-planar. Also, the channel wall region surrounding the fiber optic cable interface 13 may be polished while the remainder of the channel 11 may be non-planar. The channel walls and may comprise a hydrophilic material or coating. Contrariwise, the bottom wall of the channel 11 may comprise a hydrophobic material or coating that creates droplets suitable for spectral analysis.

The inventors have successfully experimented with the analysis channel or flow cell 10 as described herein and have developed algorithms for the spectral analysis of Urea, Creatinine Glucose, Amylase, Uric acid, and Ethanol.

Additionally, the collection receptacle 10 may include a temperature sensor such as a thermistor. Immediately following excretion, the temperature of urine is approximately equal to the temperature of the human body (37° C.) and substantially exceeds normal room temperature (25° C.). Therefore, contact with urine constitutes a signal event for the temperature sensor that can be used to identify the presence of urine in the flow cell 11. Once the presence of urine in the flow cell 11 has been identified, the spectrometer and light source 19 will be activated for sampling.

Finally, the collection device may include an integrated cleaning apparatus. This may include a spray or drip nozzle designed to release a wash solution into the flow cell to remove build-up on the surface of the flow cell or clear remaining flush water in the flow cell with a rapidly evaporating liquid such as alcohol. The cleaning apparatus may also feature a fan or compressed air nozzle designed to circulate air through the flow cell and improve clearance of residual urine, water or wash solution from the flow cell. Once the flow cell has been cleared of fluid, a timed reference scan may be initiated by the spectrometer.

The embodiment described here is provided to illustrate the function of the device and is not intended to confine the invention to a specific set of design elements, conformations or optical components. Modifications to the overall mechanical, optical or electrical design in keeping with the intent of the device may be made to improve the unit without undermining the validity of this application.

What is claimed is:

1. A specimen collection receptacle comprising:
an analysis channel disposed within a wall of a toilet bowl;
the analysis channel being open to the interior of the toilet bowl;
the specimen collection receptacle being disposed above the water line of the toilet bowl;
the analysis channel comprising opposed non-parallel side walls;
the analysis channel being in communication with a spectral analyzer; and
the specimen collection receptacle lying flush with the wall of the toilet bowl.

2. The specimen collection receptacle of claim 1, wherein the analysis channel disposed within the wall of the toilet bowl comprises reentrant side walls.

3. The specimen collection receptacle of claim 1, wherein the analysis channel disposed within the wall of the toilet bowl comprises side walls forming a truncated cone, or frusto conical, shape.

4. A specimen collection receptacle comprising:
an analysis channel disposed within a wall of a toilet bowl;
the analysis channel being open to the interior of the toilet bowl;
the specimen collection receptacle being disposed above the water line of the toilet bowl;
the specimen collection receptacle lying flush with the wall of the toilet bowl;
the analysis channel comprising opposed non-planar side walls; and
the analysis channel being in communication with a spectral analyzer.

5. The specimen collection receptacle of claim 4, wherein the non-planar side walls of the analysis channel comprise corrugations, channels, discontinuities, or protrusions.

6. The specimen collection receptacle of claim 4, wherein the analysis channel disposed within the wall of the toilet bowl comprises a fiber optic cable interface.

7. The specimen collection receptacle of claim 6, wherein the fiber optic cable interface comprises light emitting and receiving cable ends, collimating lenses, or spectral windows.

8. The specimen collection receptacle of claim 4 wherein at least a portion of the opposed non-planar side walls exhibit a polished surface.

9. The specimen collection receptacle of claim 4 wherein the opposed non-planar side walls are joined at the bottom forming a V shaped channel.

10. The specimen collection receptacle of claim 4, wherein at least a portion of the opposed non-planar side walls comprise a hydrophobic or hydrophilic coating or material.

11. The specimen collection receptacle of claim 4 wherein the opposed non-planar side walls are joined by a bottom wall.

12. The specimen collection receptacle of claim 11 wherein at least a portion of the bottom wall comprises a hydrophobic or hydrophilic material or coating.

13. The specimen collection receptacle of claim 11 wherein at least a portion of the bottom wall comprises a non-planar surface.

14. The specimen collection receptacle of claim 4, wherein the non-planar side walls of the analysis channel comprise baffles.

15. The specimen collection receptacle of claim 4, wherein the volume of the analysis channel is at least about 5 mL.

16. The specimen collection receptacle of claim 4, wherein the volume of the channel proximate the cable interface is about at least between 150 µL and 2 mL.

17. The specimen collection receptacle of claim 4, wherein the volume of the analysis channel proximate the cable interface is between 300 µL and 600 µL.

18. A specimen collection receptacle comprising:
an analysis channel disposed within a wall of a toilet bowl;
the analysis channel being open to the interior of the toilet bowl;
the specimen collection receptacle being disposed above the water line of the toilet bowl;
the analysis channel comprising opposed curvilinear side walls;
the analysis channel being in communication with a spectral analyzer; and
the specimen collection receptacle lying flush with the wall of the toilet bowl.

19. The specimen collection receptacle of claim 18, wherein the curvilinear side walls are concave or convex.

20. The specimen collection receptacle of claim 18, wherein the opposed curvilinear side walls of the analysis channel are non-planar comprising corrugations, channels, discontinuities, or protrusions.

* * * * *